(12) United States Patent
Wang et al.

(10) Patent No.: US 11,912,641 B2
(45) Date of Patent: *Feb. 27, 2024

(54) METHODS FOR REMOVAL HI/I$_2$/HI$_3$ FROM TRIFLUOROACETYL IODIDE (TFAI) FEEDSTOCK AND PYROLYSIS REACTOR EFFLUENT

(71) Applicant: Honeywell International Inc., Charlotte, NC (US)

(72) Inventors: Haiyou Wang, Amherst, NY (US); Daniel C. Merkel, Orchard Park, NY (US)

(73) Assignee: Honeywell International Inc., Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/893,504

(22) Filed: Aug. 23, 2022

(65) Prior Publication Data

US 2022/0402843 A1   Dec. 22, 2022

Related U.S. Application Data

(63) Continuation of application No. 17/495,511, filed on Oct. 6, 2021, now Pat. No. 11,453,631.

(60) Provisional application No. 63/091,727, filed on Oct. 14, 2020.

(51) Int. Cl.
  *C07C 51/47* (2006.01)
  *C07C 17/389* (2006.01)
  *C07C 17/18* (2006.01)

(52) U.S. Cl.
  CPC ............ *C07C 17/389* (2013.01); *C07C 17/18* (2013.01); *C07C 51/47* (2013.01)

(58) Field of Classification Search
  CPC ...................................................... C07C 51/64
  See application file for complete search history.

(56) References Cited

U.S. PATENT DOCUMENTS

| | | | |
|---|---|---|---|
| 5,892,136 A | 4/1999 | Nagasaki et al. | |
| 7,196,236 B2 * | 3/2007 | Mukhopadhyay | .... C07C 17/093 570/174 |
| 2006/0122440 A1 | 6/2006 | Mukhopadhyay et al. | |
| 2020/0062678 A1 | 2/2020 | Nair et al. | |
| 2020/0062679 A1 * | 2/2020 | Nair | .................... B01J 35/0006 |
| 2020/0172457 A1 * | 6/2020 | Jungong | ............... C07C 17/395 |
| 2022/0112144 A1 | 4/2022 | Wang et al. | |

FOREIGN PATENT DOCUMENTS

CN     103524325 A     1/2014

OTHER PUBLICATIONS

International Search Report and Written Opinion received for PCT Patent Application No. PCT/US2021/071842, dated Jan. 28, 2022, 9 pages.

* cited by examiner

*Primary Examiner* — Medhanit W Bahta
(74) *Attorney, Agent, or Firm* — Faegre Drinker Biddle & Reath LLP

(57) ABSTRACT

A method of producing trifluoroiodomethane (CF$_3$I) includes providing a feedstock comprising trifluoroacetyl iodide (TFAI), passing the feedstock through at least one column charged with carbonaceous materials to remove hydrogen iodide (HI), hydrogen triiodide (HI$_3$) and iodine (I$_2$) from the feedstock, and providing the feedstock to a reactor to produce a trifluoroiodomethane product stream. Another method of producing trifluoroiodomethane (CF$_3$I) includes providing a feedstock comprising trifluoroacetyl iodide (TFAI) to a reactor to produce a trifluoroiodomethane product stream, and passing the trifluoroiodomethane product stream from the reactor through at least one column charged with carbonaceous materials to remove hydrogen iodide (HI), hydrogen triiodide (HI3) and iodine (I2) from the trifluoroiodomethane product stream.

20 Claims, 2 Drawing Sheets

METHODS FOR REMOVAL HI/I₂/HI₃ FROM TRIFLUOROACETYL IODIDE (TFAI) FEEDSTOCK AND PYROLYSIS REACTOR EFFLUENT

CROSS-REFERENCE TO RELATED APPLICATIONS

This application is a continuation application of U.S. patent application Ser. No. 17/495,511, filed Oct. 6, 2021, which claims priority to Provisional Application No. 63/091,727, filed Oct. 14, 2020, both of which are herein incorporated by reference in their entireties.

FIELD

The present disclosure relates to processes for producing trifluoroiodomethane ($CF_3I$). Specifically, the present disclosure relates to methods for removing hydrogen- and iodine-containing species from trifluoroacetyl iodide (TFAI) feedstock and from the reactor effluent stream to improve the process for producing trifluoroiodomethane from trifluoroacetyl iodide (TFAI).

BACKGROUND

Trifluoroiodomethane ($CF_3I$), also known as perfluoromethyliodide, trifluoromethyl iodide, or iodotrifluoromethane, is a useful compound in commercial applications, as a refrigerant or a fire suppression agent, for example. Trifluoroiodomethane ($CF_3I$) is an environmentally acceptable compound with a low global warming potential and low ozone depletion potential. Trifluoroiodomethane ($CF_3I$) can replace more environmentally damaging materials.

Methods of preparing trifluoroiodomethane are known. For example, U.S. Pat. No. 7,132,578 (Mukhopadhyay et al.) discloses a catalytic, one-step process for producing trifluoroiodomethane from trifluoroacetyl chloride. However, the source of iodine, is iodine fluoride (IF). Iodine fluoride is relatively unstable, decomposing above 0° C. to $I_2$ and $IF_5$. Iodine fluoride may also not be available in commercially useful quantity.

In another example, U.S. Pat. No. 7,196,236 (Mukhopadhyay et al.) discloses a catalytic process for producing trifluoroiodomethane using reactants comprising a source of iodine, such as hydrogen iodide, at least a stoichiometric amount of oxygen, and a reactant $CF_3R$, where R is selected from the group consisting of —COOH, —COX, —CHO, —COOR₂, AND —SO₂X, where $R_2$ is alkyl group and X is a chlorine, bromine, or iodine. Hydrogen iodide, which may be produced by the reaction, is oxidized by the at least a stoichiometric amount of oxygen, producing water and iodine for economic recycling. Several other processes are referenced in the literature for making trifluoroiodomethane ($CF_3I$) from trifluoroacetyl chloride with hydrogen iodide in a vapor phase reaction.

In yet another example, U.S. patent application Ser. No. 16/549,412 discloses a two-step process for producing trifluoroiodomethane from trifluoroacetyl chloride. The process consists of a first step of making trifluoroacetyl iodide via the reaction of $CF_3COCl + HI \rightarrow CF_3COI + HCl$ and a second step of making trifluoroiodomethane via the reaction of $CF_3COI \rightarrow CF_3I + CO$. This process provides higher selectivity to trifluoroiodomethane ($CF_3I$) than others.

While developing the above two-step process, the applicants found one, two, or all three impurities of HI, $I_2$, and $HI_3$ were present, even in purified trifluoroacetyl iodide (TFAI) feed material. During the conversion step of trifluoroacetyl iodide (TFAI) to trifluoroiodomethane ($CF_3I$), the presence of these hydrogen-containing species, such as HI and $HI_3$, resulted in increased formation of some by-products such as $CF_3H$ (HFC-23). Furthermore, the presence of iodine-containing species, such as $I_2$ and $HI_3$, together with additional $I_2$ formed during the reaction, caused increased corrosion of equipment and/or operational difficulties including flow, pressure control and plugging issues. These results are disadvantageous from the standpoints of reduced productivity of the desired product and an increased operational cost. Hence, there is a need for a means to remove $HI/I_2/HI_3$ from trifluoroacetyl iodide (TFAI) feedstock, and $I_2$ from the Step 2 reactor effluent stream.

SUMMARY

The present disclosure provides methods for the production of trifluoroiodomethane ($CF_3I$) from a feedstock including trifluoroacetyl iodide (TFAI).

In one embodiment, the present invention provides a method of producing trifluoroiodomethane ($CF_3I$) including providing a feedstock comprising trifluoroacetyl iodide (TFAI), passing the feedstock through at least one column charged with carbonaceous materials to remove hydrogen iodide (HI). hydrogen triiodide ($HI_3$) and iodine ($I_2$) from the feedstock, and providing the feedstock to a reactor to produce a trifluoroiodomethane product stream.

In another embodiment, the present invention provides a method of producing trifluoroiodomethane ($CF_3I$) including providing a feedstock comprising trifluoroacetyl iodide (TFAI), providing the feedstock to a reactor to produce a trifluoroiodomethane product stream, and passing the trifluoroiodomethane product stream from the reactor through at least one column charged with carbonaceous materials to remove hydrogen iodide (HI), hydrogen triiodide ($HI_3$) and iodine ($I_2$) from the trifluoroiodomethane product stream.

The above mentioned and other features of the disclosure, and the manner of attaining them, will become more apparent and will be better understood by reference to the following description of embodiments

DETAILED DESCRIPTION

Figure 1:
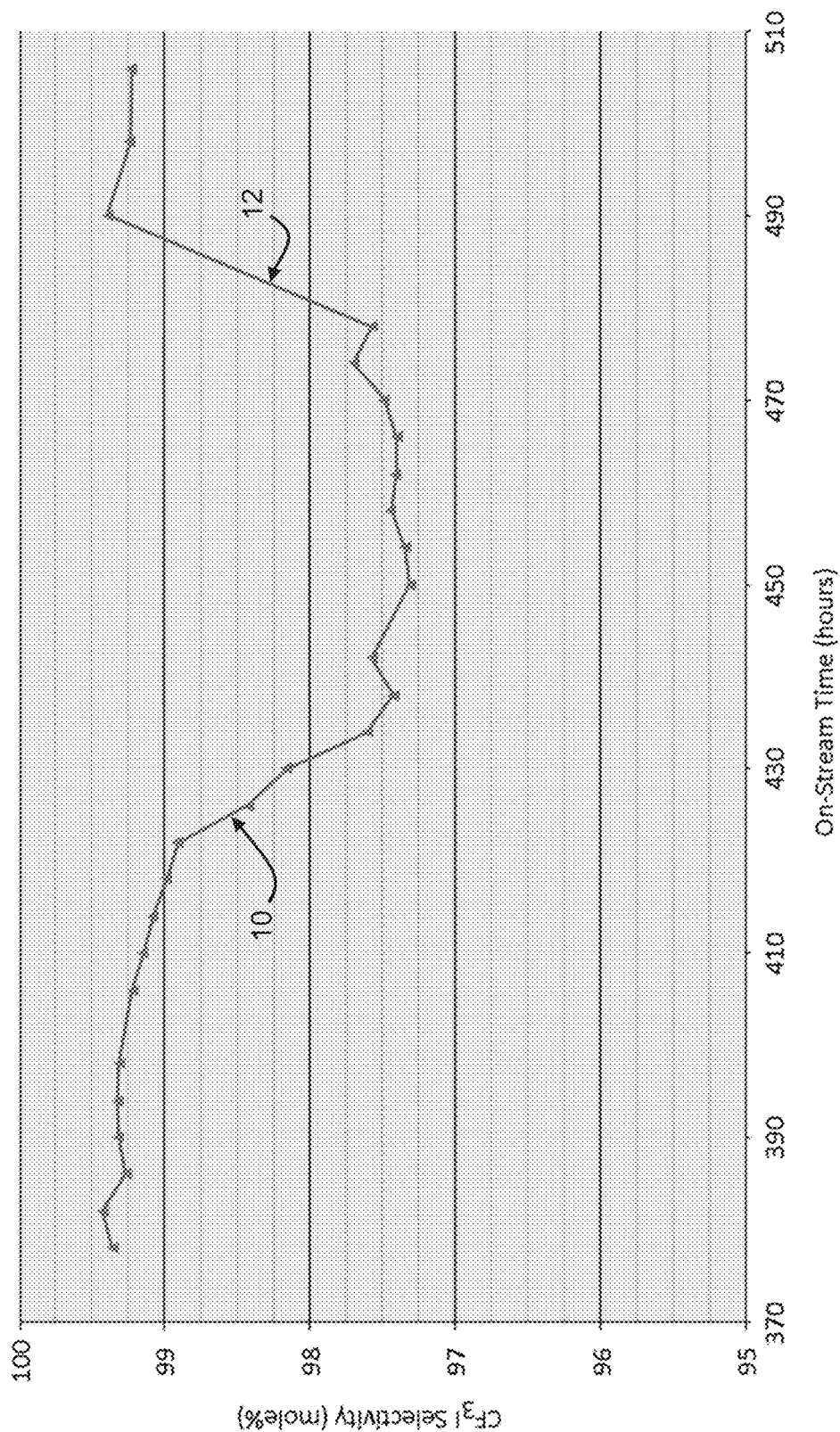
FIG. 1 shows changes in selectivity for trifluoroiodomethane ($CF_3I$) with spent activated carbon columns and fresh activated carbon columns.

The present disclosure provides methods for removing hydrogen- and iodine-containing species from trifluoroacetyl iodide (TFAI) feedstock and from the reactor effluent stream during conversion of trifluoroacetyl iodide (TFAI) to trifluoroiodomethane ($CF_3I$).

As disclosed in U.S. patent application Ser. No. 16/549,412, trifluoroiodomethane ($CF_3I$) can be formed via the decomposition of trifluoroacetyl iodide (TFAI) according to Equation 1 below:

$$CF_3COI \rightarrow CF_3I + CO. \quad \text{Eq. 1:}$$

The reaction can take place in a heated tube reactor comprising a tube made of a metal such as stainless steel, nickel, and/or a nickel alloy, such as a nickel-chromium alloy, a nickel-molybdenum alloy, a nickel-chromium-molybdenum alloy, or a nickel-copper alloy. The tube within the reactor may be heated. The reactor may also include any type of packed bed reactor. The packing may be a catalyst or an inert material that improves heat transfer and promotes mixing of the reactants and products.

The reaction may be carried out at a temperature of about 200° C. or greater, about 250° C. or greater, about 300° C. or greater, about 350° C. or greater, about 400° C. or lower, about 450° C. or lower, about 500° C. or lower, about 550° C. or lower, about 600° C. or lower, or within any range encompassing these endpoints. Preferably, the temperature is about 300° C. to about 500° C. More preferably, the temperature is about 350° C. to about 450° C.

The reaction may be carried out at a pressure of about 0 psig or greater, about 5 psig or greater, about 20 psig or greater, about 50 psig or greater, about 70 psig or greater, about 100 psig or greater, about 150 psig or lower, about 200 psig or lower, about 225 psig or lower, about 250 psig or lower, about 275 psig or lower, about 300 psig, or within any range encompassing these endpoints. Preferably, the reaction is carried out at a pressure of about 5 psig to about 275 psig. More preferably, the reaction is carried out at a pressure of about 10 psig to about 250 psig.

The contact time of the reaction may be about 0.1 second or greater, about 1 second or greater, about 5 seconds or greater, about 10 seconds or greater, about 60 seconds or greater, about 100 seconds or less, about 150 seconds or less, about 200 seconds or less, about 250 seconds or less, about 300 seconds or less, about 600 seconds or less or within any range encompassing these endpoints. Preferably, the contact time of the reaction is about 0.1 seconds to about 60 seconds. More preferably, the contact time of the reaction is about 0.1 seconds to about 10 seconds.

The reaction may be conducted in the presence of a catalyst. The catalyst may comprise stainless steel, nickel, nickel-chromium alloy, nickel-chromium-molybdenum alloy, nickel-copper alloy, copper, alumina, silicon carbide, platinum, palladium, rhenium, activated carbon, such as such as Norit PK 3-5, Calgon or Shirasagi carbon, or combinations thereof. Alternatively, the reaction may be conducted in the absence of a catalyst.

Not wishing to be bound by or to any particular theory of operation, certain aspects of the present disclosure are based on the observation and understanding that, during the reaction, the presence of certain hydrogen-containing species including HI and HI$_3$ resulted in increased formation of some by-products such as CF$_3$H (HFC-23) and iodine (I$_2$) according to Equation 2 below:

$$CF_3COI + HI/HI_3 \rightarrow CF_3H + CO + I_2. \qquad \text{Eq. 2:}$$

The formation of trifluoromethane (CF$_3$H) is undesired as it inevitably leads to decreased yield of the trifluoroiodomethane (CF$_3$I) target product. The iodine (I$_2$) present in the trifluoroacetyl iodide (TFAI) feed stream, formed via the above side reaction during the decomposition of trifluoroacetyl iodide (TFAI), is likewise undesirable, as it causes increased corrosion of equipment and operational issues such as plugging when solid iodine (I$_2$) forms.

It has been found hydrogen- and iodine-containing species including HI, HI$_3$, and I$_2$ could be reduced and/or removed from the trifluoroacetyl iodide (TFAI) feed stream as well as the reactor effluent stream via an adsorption process over carbonaceous materials. This process results in improved selectivity for trifluoroacetyl iodide (CF$_3$I) over trifluoromethane (CF$_3$H) and reduced operational issues such as plugging.

The present disclosure provides a method wherein at least one column charged with carbonaceous materials is used. This column may be positioned such that hydrogen- and iodine-containing species, such as HI, HI$_3$ and I$_2$, may be removed from the trifluoroacetyl iodide (TFAI) feedstock prior to entering the reactor to form trifluoroiodomethane (CF$_3$I) as shown in Equation 1, above. Without being bound by theory, removing these species from the trifluoroiodomethane feedstock may limit undesired side reactions leading to the formation of trifluoromethane (CF$_3$H), as shown in Equation 2. Thus, the selectivity of the reaction for the desired trifluoroiodomethane (CF$_3$I) may be improved. Furthermore, formation of iodine (I$_2$) may be limited, thereby limiting operational issues, such as plugging and corrosion.

In one embodiment, at least one column charged with carbonaceous materials is installed such that the trifluoroacetyl iodide (TFAI) feedstock can be recirculated through it prior to being fed to the reactor. In another embodiment, at least one column charged with carbonaceous materials is installed in the trifluoroacetyl iodide (TFAI) feed line and the trifluoroacetyl iodide (TFAI) feed is passed through it prior to being fed to the reactor. In yet another embodiment, at least one column charged with carbonaceous materials is installed such that the trifluoroacetyl iodide (TFAI) feedstock can be recirculated through it prior to being fed to the reactor, and at least one column charged with carbonaceous materials is installed in the trifluoroacetyl iodide (TFAI) feed line and the trifluoroacetyl iodide (TFAI) feed is passed through it prior to being fed to the reactor.

The trifluoroacetyl iodide (TFAI) passed through the at least one column charged with carbonaceous materials before being fed to the reactor may be in liquid form, vapor form, or any combination of the two. Preferably, the TFAI is in liquid form. The column is operated at a temperature as low as about 0° C., about 10° C., about 20° C., about 30° C. or about 40° C., or as high as about 50° C., about 60° C., about 70° C., about 80° C., about 90° C. or about 100° C., or within any range defined between any two of the foregoing values, such as about 0° C. to about 100° C., about 10° C. to about 90° C., about 20° C. to about 80° C., about 30° C. to about 70° C., about 40° C. to about 60° C., about 50° C. to about 70° C., about 40° C. to about 50° C., about 60° C. to about 90° C., about 0° C. to about 60° C. or about 20° C. to about 40° C., for example. Preferably, the column is operated at a temperature of about 0° C. to about 60° C. More preferably, the column is operated at a temperature of about 20° C. to about 40° C.

The column is operated at a pressure slightly above the reactor pressure or at a pressure of as low as about 0 psig, about 5 psig, about 20 psig, about 50 psig, about 70 psig or about 100 psig, or as high as about 150 psig, about 200 psig, about 250 psig or about 300 psig, or within any range defined between any two of the foregoing values, such as about 0 psig to about 300 psig, about 5 psig to about 250 psig, about 20 psig to about 200 psig, about 50 psig to about 150 psig, about 5 psig to about 100 psig, about 20 psig to about 70 psig, or about 150 psig to about 250 psig, for example. Preferably, the column is operated at a pressure of about 5 psig to about 250 psig. More preferably, the column is operated at a pressure of about 10 psig to about 100 psig.

When the trifluoroacetyl iodide (TFAI) is passed through the at least one column charged with carbonaceous materials prior to being fed to the reactor, a stable and controllable flow of trifluoroacetyl iodide (TFAI) may be achieved. Furthermore, higher selectivity for trifluoroiodomethane (CF$_3$I) versus trifluoromethane (CF$_3$H) may be achieved in comparison to methods not employing the at least one column charged with carbonaceous materials.

The present disclosure further provides a method wherein at least one additional column charged with carbonaceous materials is installed in a reactor effluent line. Specifically, a first column charged with carbonaceous materials is installed such that hydrogen- and iodine-containing species, such as hydrogen iodide (HI), hydrogen triiodide ($HI_3$) and iodine ($I_2$), may be removed from the trifluoroacetyl iodide (TFAI) feedstock prior to entering the reactor, as described above, and a second column charged with carbonaceous materials is installed in the reactor effluent line. In this method, the first column may be installed in the trifluoroacetyl iodide (TFAI) feed line to remove hydrogen- and iodine-containing species, and a second column may be installed in the reactor effluent line to remove hydrogen- and iodide-containing species, including iodine ($I_2$), from the desired trifluoroiodomethane ($CF_3I$) product stream. The iodine ($I_2$) may be additionally formed during the course of undesired side reactions, as shown in Equation 2. Removal of the iodine ($I_2$) by passing the reactor effluent stream through a column charged with carbonaceous materials may prevent the formation of solid iodine ($I_2$), thereby limiting operational issues such as plugging and corrosion of equipment.

In this method, the first column is operated at as described above, and the second column is operated at a temperature as low as about 0° C., about 10° C., about 20° C., about 30° C. or about 40° C., or as high as about 50° C., about 60° C., about 70° C., about 80° C., about 90° C. or about 100° C., or within any range defined between any two of the foregoing values, such as about 0° C. to about 100° C., about 10° C. to about 90° C., about 20° C. to about 80° C., about 30° C. to about 70° C., about 40° C. to about 60° C., about 50° C. to about 70° C., about 40° C. to about 50° C., about 60° C. to about 90° C., about 40° C. to about 80° C. or about 50° C. to about 70° C., for example. Preferably, the second column is operated at a temperature of about 40° C. to about 80° C. More preferably, the second column is operated at a temperature of about 50° C. to about 70° C.

The present disclosure further provides a method wherein at least one column charged with carbonaceous materials is installed in the reactor effluent line, as described above. The column is operated as described above. In this method, there is no column positioned such that hydrogen- and iodine-containing species, such as HI, $HI_3$ and $I_2$ may be removed from the trifluoroacetyl iodide (TFAI) feedstock prior to entering the reactor.

Suitable carbonaceous materials may include activated carbons, carbon blacks, and carbon molecular sieves. When activated carbons are used, those with an iodine number higher than 500 (surface area greater than 900 m²/g)) are preferred. The iodine number may be determined, for example, by ASTM D4607. When carbon blacks are used, those with an iodine number higher than 500 (surface area greater than 400 m²/g)) are preferred. The iodine number may be determined, for example, by ASTM D1510-16. When carbon molecular sieves are used, those with an average pore size greater than 2 Å are preferred.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

As used herein, the modifier "about" used in connection with a quantity is inclusive of the stated value and has the meaning dictated by the context (for example, it includes at least the degree of error associated with the measurement of the particular quantity). When used in the context of a range, the modifier "about" is also considered as disclosing the range defined by the absolute values of the two endpoints.

The following non-limiting Examples serve to illustrate the disclosure.

EXAMPLES

Example 1: Analysis of Treated Trifluoroacetyl Iodide (TFAI)

A 1-inch outer diameter by 9-inch length stainless steel column was charged with 29.2 g fresh Norit ROX 0.8 activated carbon having an iodine number of 1,100 and a BET surface area of 1,225 m²/g. Two 300 mL collection cylinders were prepared. The first cylinder was connected to the exit of the trifluoroacetyl iodide (TFAI) feed line and placed in a Dewar filled with wet ice and set on a balance. The flow of TFAI was started at 0.25 lb/hr and was passed through the activated carbon (AC) column at room temperature. The flow was then directed to a scrubber carboy until liquid was observed entering the carboy, indicating that the entire feed line was liquid-filled. Next, the feed flow path was switched over to the collection cylinder for about 3 hours for a total of about 0.75 pounds as confirmed by the weight increase on the balance. The cylinder was isolated and replaced by the second cylinder, and the flow of TFAI was restarted to the new collection cylinder. The two collection cylinders of TFAI, together with a cylinder of pristine TFAI feed, were subjected to various analyses including $I_2$ titration and $^1$H NMR.

Iodine concentration was determined by adding a sample to 36 grams DI water, mixing, adding 4.0 grams KI, mixing and titrating with sodium thiosulfate. The concentration of hydrogen- and iodine-containing species was determined by Proton NMR ($^1$H-NMR) method by transferring a sample to a heavy wall, valved, NMR tube containing deuterated chloroform ($CDCl_3$) with calibrated tetramethylsilane (TMS) standard. The concentrations of identified components in the sample were calculated based on the integration values of their peaks. A 300 MHz field strength was used for the analysis of the samples.

The concentrations of $I_2$ as well as other hydrogen- and iodine-containing species such as HI and $HI_3$ were compared before and after treatment with the activated carbon (AC) column. The results of these analyses are shown below in Table 1.

TABLE 1

| Species | Before AC column (ppm) | After AC column (ppm) | |
|---|---|---|---|
| | | Collection cylinder 1 | Collection cylinder 2 |
| $I_2$ | 2883 | 2029 | 1751 |
| HI | 1903 | 0 | 241 |
| $HI_3$ | 632 | 231 | 209 |

Example 2—Changes in Selectivity with Spent and Fresh Activated Carbon

The selectivity for trifluoroiodomethane ($CF_3I$) and trifluoromethane ($CF_3H$) was tested using spent and fresh activated carbon. While continuously running the decomposition reaction of Eq.1 above under conditions of 390° C., 25 psig, 0.25 lb/h, 2.4 sec (contact time), the concentration of hydrogen-containing impurities in the trifluoroacetyl iodide (TFAI) feedstock was reduced by passing liquid trifluoroacetyl iodide (TFAI) through a column filled with 29.4 g Norit ROX 0.8 activated carbon (AC) at room temperature. The AC was able to absorb hydrogen-containing impurities, such as HI and $HI_3$, from the TFAI feedstock and increase the selectivity for the desired trifluoroiodomethane ($CF_3I$) product while minimizing the formation of trifluoromethane ($CF_3H$). Once the activated carbon was spent, hydrogen-containing impurities in the trifluoroacetyl iodide (TFAI) feedstock, such as HI and $HI_3$, were fed to the reactor along with the feedstock. The selectivity for trifluoromethane ($CF_3I$) then decreased by about 2% once the AC column was spent, as indicated in FIG. 1 at section 10. Once the spent AC was replaced with fresh AC, the selectivity for trifluoromethane ($CF_3I$) immediately returned to its original level, as indicated in FIG. 1 at section 12.

Figure 2:
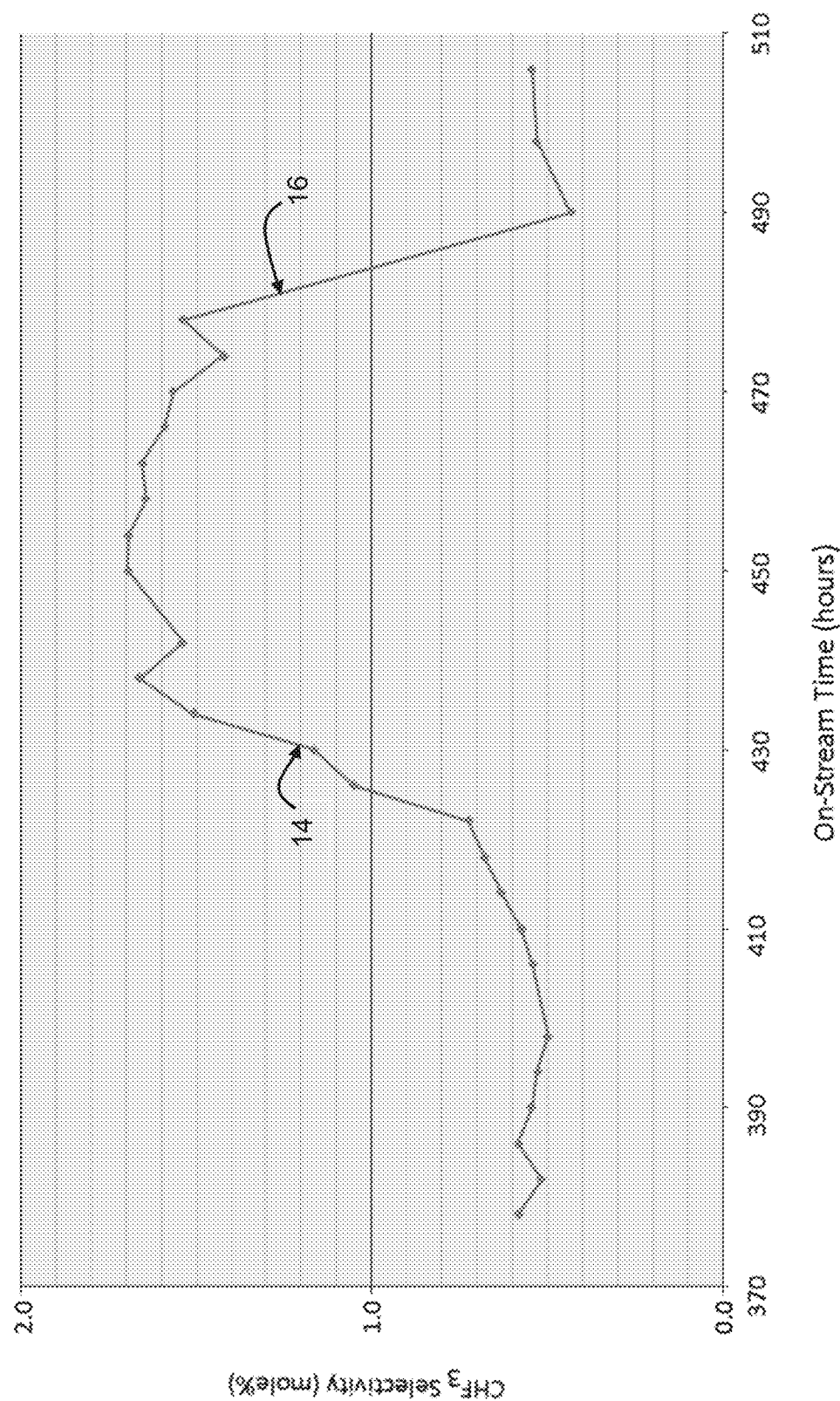
FIG. 2 shows changes in selectivity for trifluoromethane ($CF_3H$) with spent activated carbon columns and fresh activated carbon columns.

The formation of trifluoromethane ($CF_3H$) increased by about 1.1% once the AC was spent, as indicated in FIG. 2 at section 14. After the spent AC was replaced with fresh AC, the selectivity for trifluoromethane ($CF_3H$) immediately returned to its original level, as indicated in FIG. 2 at section 16.

Example 3—Effects of Filtered Feed Stock on Product Selectivity

Next, the effects of using activated carbon (AC) to remove hydrogen-containing impurities, such as HI and $HI_3$, as well as iodine ($I_2$) from the trifluoroacetyl iodide (TFAI) was tested. The decomposition reaction according to Eq. 1 above was conducted at 300° C., 25 psig, 0.25 lb/h TFAI feed rate, and 4.9 sec contact time. A 1-inch outer diameter by 9-inch length stainless steel column was charged with 29.5 grams of fresh Norit ROX 0.8 activated carbon (AC) was installed in the trifluoroacetyl iodide (TFAI) feed line, along with a by-pass loop around the column. The liquid trifluoroacetyl iodide (TFAI) feed was passed through the column at room temperature ("on stream"). The reactor and the reactor effluent gas chromatography (GC) data was collected over 48 hours. The average selectivity for trifluoroiodomethane ($CF_3I$) was 99.62%. The main by-product was trifluoromethane ($CF_3H$).

Next, the same trifluoroacetyl iodide (TFAI) feedstock was left untreated (i.e., bypassing the AC column, "bypass"), and was used as feed for about 48 hours under the same reaction conditions described above. The average selectivity for trifluoroiodomethane ($CF_3I$) decreased to 99.33%, while selectivity for the same major impurity (trifluoromethane, $CF_3H$) increased.

The experiment was repeated with a different trifluoroacetyl iodide (TFAI) feedstock and the same trend was observed. Results of the tests can be found below in Table 2. The tests show that the use of AC column installed on the trifluoroacetyl iodide (TFAI) feed line resulted in improved selectivity for trifluoroiodomethane ($CF_3I$), while trifluoroacetyl iodide (TFAI) conversion remained at comparable levels.

TABLE 2

| Exp. # | AC column | TFAI conv., % | Product selectivity, mol % | | |
|---|---|---|---|---|---|
| | | | $CF_3I$ | $CF_3H$ | Others* |
| 1 | On stream | 66.043 | 99.619 | 0.261 | 0.120 |
| | Bypassed | 65.164 | 99.330 | 0.435 | 0.235 |
| 2 | On stream | 69.154 | 99.346 | 0.402 | 0.252 |
| | Bypassed | 69.608 | 98.924 | 0.678 | 0.398 |

*Others include trifluoroacetyl fluoride, $C_2F_5I$, etc.

The activated carbon column used in Example 2 was removed from the trifluoroacetyl iodide (TFAI) line, and the AC was discharged and weighed. After being used, its weight was 2.7 times its original weight, indicating it had adsorbed significant amounts of species present in the trifluoroacetyl iodide (TFAI) feed. The AC was further analyzed by means of TGA-MS (Thermogravimetric Analysis-Mass Spectrometry) to determine the nature of adsorbed species. As shown in Table 3, the species desorbed during TGA include $I_2$, HI, and trifluoroacetyl iodide (TFAI). The absence of $HI_3$ among the detected species could be due to its instability upon heating, during which it may decompose to deposed to HI and iodine ($I_2$).

TABLE 3

| Analyte | m/z | Peak Intensity* | Notes |
|---|---|---|---|
| $CF_3$ | 69 | 8.36E−11 | $CF_3$ fragment |
| I | 127 | 7.78E−10 | I fragment |
| HI | 128 | 1.98E−11 | HI molecule |
| $CF_3I$ | 196 | 1.80E−11 | $CF_3I$ molecule or TFAI fragment** |
| $I_2$ | 254 | 8.12E−10 | $I_2$ molecule |

*The larger the peak intensity, the higher the concentration of the analyte.
**This is more likely representative of a $CF_3I$ fragment from the TFAI molecule, given that the TFAI feed was passed through the AC column.

These results, together with the results from Example 1, indicate that AC can be used to remove $I_2$, HI, and $HI_3$ from trifluoroacetyl iodide (TFAI) feedstock.

Example 4—Effects of Filtered Feedstock in Conjunction with Filtered Effluent The reaction was performed under the same conditions described in Example 3, with the activated carbon (AC) column installed on the trifluoroacetyl iodide (TFAI) feed line as described in Example 3. While running the reaction, the reactor exit piping was becoming restricted with solid $I_2$ crystals (precipitated from the vapor reactor effluent stream) every 38 hours on average. A column packed with Norit ROX 0.8 activated carbon (AC) was installed in the reactor exit line and was kept at 60° C. during operation with no change to the remaining conditions. In this case, the average time prior to iodine crystal-induced restrictions in the reactor exit piping was increased to over 100 hours due to adsorption of iodine ($I_2$) by the AC.

The activated carbon column used above was removed from the reactor exit line and the spent AC was analyzed by means of TGA-MS (Thermogravimetric Analysis-Mass Spectrometry) to determine the nature of adsorbed species. As shown in Table 4, the species desorbed during TGA include $I_2$, HI, and trifluoroacetyl iodide (TFAI). The absence of $HI_3$ among the detected species could be due to its instability upon heating, during which it may decompose to HI and iodine ($I_2$).

TABLE 4

| Analyte | m/z | Peak Intensity* | Notes |
|---|---|---|---|
| $CF_3$ | 69 | 1.94E−11 | $CF_3$ fragment |
| I | 127 | 1.23E−9 | I fragment |
| HI | 128 | 9.01E−11 | HI molecule |
| $CF_3I$ | 196 | 7.98E−12 | $CF_3I$ molecule and/or TFAI fragment** |
| $I_2$ | 254 | 1.63E−9 | $I_2$ molecule |

*The larger the peak intensity, the higher the concentration of the analyte.
**This is likely representative of both $CF_3I$ molecules and TFAI fragments, as both $CF_3I$ and TFAI were present in the reactor effluent stream.

These results, together with the results from Example 1, indicate that AC can be used to remove $I_2$, HI, and $HI_3$ from the reactor effluent stream when converting trifluoroacetyl iodide (TFAI) to trifluoroiodomethane ($CF_3I$).

Example 5: Effect of Filtered Effluent

In this Example, a column charged with activated carbon (AC) column is not installed on the trifluoroacetyl iodide (TFAI) feed line as described in Example 3. A column is packed with Norit ROX 0.8 activated carbon (AC) and is installed in the reactor exit line. The reactor exit line may be kept at 60° C. during operation with no change to the remaining conditions. Thus, the average time prior to iodine crystal-induced restrictions in the reactor exit piping may be increased due to adsorption of iodine ($I_2$) by the AC.

ASPECTS

Aspect 1 is a method of producing trifluoroiodomethane ($CF_3I$). The method comprises providing a feedstock comprising trifluoroacetyl iodide (TFAI), passing the feedstock through at least one column charged with carbonaceous materials to remove hydrogen iodide (HI), hydrogen triiodide ($HI_3$) and iodine ($I_2$) from the feedstock, and providing the feedstock to a reactor to produce a trifluoroiodomethane product stream.

Aspect 2 is the method of Aspect 1, wherein passing the feedstock through at least one column charged with carbonaceous materials comprises passing the feedstock through the at least one column immediately prior to providing the feedstock to a reactor.

Aspect 3 is the method of Aspect 1, wherein passing the feedstock through at least one column charged with carbonaceous materials comprises recirculating the feedstock through the at least one column before providing the feedstock to the reactor.

Aspect 4 is the method of Aspect 1, wherein the at least one column charged with carbonaceous materials includes at least two columns and passing the feedstock through at least one column charged with carbonaceous materials comprises recirculating the feedstock through one of the two columns and then passing the feedstock through the other of the two columns immediately prior to providing the feedstock to a reactor.

Aspect 5 is the method of any of Aspects 1-4, wherein the at least one column is operated at a temperature of about 0° C. to about 100° C.

Aspect 6 is the method of any of Aspects 1-4, wherein the at least one column is operated at a temperature of about 0° C. to about 60° C.

Aspect 7 is the method of any of Aspects 1-4, wherein the at least one column is operated at a temperature of about 20° C. to about 40° C.

Aspect 8 is the method of any of Aspects 1-7, wherein the at least one column is operated at a pressure of about 0 psig to about 300 psig.

Aspect 9 is the method of any of Aspects 1-7, wherein the at least one column is operated at a pressure of about 5 psig to about 250 psig.

Aspect 10 is the method of any of Aspects 1-7, wherein the at least one column is operated at a pressure of about 10 psig to about 100 psig.

Aspect 11 is the method of and of Aspects 1-10, wherein the carbonaceous materials are selected from the group consisting of: activated carbon, carbon black, and carbon molecular sieves.

Aspect 12 is the method of Aspect 11, wherein the carbonaceous materials comprise activated carbon having an iodine number of at least 500 and a surface area of at least 900 $m^2/g$.

Aspect 13 is the method of Aspect 11, wherein the carbonaceous materials comprise carbon black having an iodine number of at least 500 and a surface area of at least 400 $m^2/g$.

Aspect 14 is the method of Aspect 11, wherein the carbonaceous materials comprise carbon molecular sieves have a pore size of at least about 2 Å.

Aspect 15 is the method of any of Aspects 1-14, wherein at least one column charged with carbonaceous materials is at least one first column, the method further comprising passing the trifluoroiodomethane product stream from the reactor through at least one second column charged with carbonaceous materials to remove hydrogen iodide (HI), hydrogen triiodide ($HI_3$) and iodine ($I_2$) from the trifluoroiodomethane product stream.

Aspect 16 is the method of Aspect 15, wherein the at least one first column is operated at a temperature of about 0° C. to about 100° C. and the second column is operated at a temperature of about 0° C. to about 100° C.

Aspect 17 is the method of Aspect 15, wherein the at least one first column is operated at a temperature of about 0° C. to about 60° C. and the second column is operated at a temperature of about 40° C. to about 80° C.

Aspect 18 is the method of Aspect 15, wherein the at least one first column is operated at a temperature of about 20° C. to about 40° C. and the second column is operated at a temperature of about 50° C. to about 70° C.

Aspect 19 is the method of any of Aspects 15-18, wherein the carbonaceous materials in the at least one second column are chosen from the group consisting of: activated carbon, carbon black, and carbon molecular sieves.

Aspect 20 is the method of Aspect 19, wherein the carbonaceous materials in the at least one second column comprise activated carbon having an iodine number of at least 500 and a surface area of at least 900 $m^2/g$.

Aspect 21 is the method of Aspect 19, wherein the carbonaceous materials in the at least one second column comprise carbon black having an iodine number of at least 500 and a surface area of at least 400 $m^2/g$.

Aspect 22 is the method of Aspect 19, wherein the carbonaceous materials in the at least one second column comprise carbon molecular sieves have a pore size of at least about 2 Å.

Aspect 23 is a method of producing trifluoroiodomethane ($CF_3I$). The method comprises providing a feedstock comprising trifluoroacetyl iodide (TFAI); providing the feedstock to a reactor to produce a trifluoroiodomethane product stream; and passing the trifluoroiodomethane product stream from the reactor through at least one column charged with carbonaceous materials to remove hydrogen iodide (HI), hydrogen triiodide ($HI_3$) and iodine ($I_2$) from the trifluoroiodomethane product stream.

Aspect 24 is the method of Aspect 23, wherein the at least one column is operated at a temperature of about 0° C. to about 100° C.

Aspect 25 is the method of Aspect 23, wherein the at least one column is operated at a temperature of about 40° C. to about 80° C.

Aspect 26 is the method of Aspect 23, wherein the at least one column is operated at a temperature of about 50° C. to about 70° C.

Aspect 27 is the method of any of Aspects 23-26, wherein the carbonaceous materials are chosen from the group consisting of: activated carbon, carbon black, and carbon molecular sieves.

Aspect 28 is the method of Aspect 27, wherein the carbonaceous materials comprise activated carbon having an iodine number of at least 500 and a surface area of at least 900 $m^2/g$.

Aspect 29 is the method of Aspect 27, wherein the carbonaceous materials comprise carbon black having an iodine number of at least 500 and a surface area of at least 400 $m^2/g$.

Aspect 30 is the method of Aspect 27, wherein the carbonaceous materials comprise carbon molecular sieves have a pore size of at least about 2 Å.

Aspect 31 is a method of producing trifluoroiodomethane ($CF_3I$). The method comprises providing a feedstock comprising trifluoroacetyl iodide (TFAI), passing the feedstock through at least one column charged with carbonaceous materials to remove hydrogen iodide (HI), hydrogen triiodide ($HI_3$) and iodine ($I_2$) from the feedstock, and providing the feedstock to a reactor to produce a trifluoroiodomethane product stream. The at least one column is operated at a temperature of about 20° C. to about 40° C. The at least one column is operated at a pressure of about 10 psig to about 100 psig. The carbonaceous materials comprise activated carbon having an iodine number of at least 500 and a surface area of at least 900 $m^2/g$, carbon black having an iodine number of at least 500 and a surface area of at least 400 $m^2/g$, or carbon molecular sieves have a pore size of at least about 2 Å.

Aspect 32 is the method of Aspect 31, wherein passing the feedstock through at least one column charged with carbonaceous materials comprises passing the feedstock through the at least one column immediately prior to providing the feedstock to a reactor, passing the feedstock through at least one column charged with carbonaceous materials comprises recirculating the feedstock through the at least one column before providing the feedstock to the reactor, or passing the feedstock through at least one column charged with carbonaceous materials comprises recirculating the feedstock through one of two columns and then passing the feedstock through another of the two columns immediately prior to providing the feedstock to a reactor.

Aspect 33 is the method of Aspect 31 or Aspect 32, wherein at least one column charged with carbonaceous materials is at least one first column, the method further comprising passing the trifluoroiodomethane product stream from the reactor through at least one second column charged with carbonaceous materials to remove hydrogen iodide (HI), hydrogen triiodide ($HI_3$) and iodine ($I_2$) from the trifluoroiodomethane product stream. The at least one first column is operated at a temperature of about 20° C. to about 40° C. and the second column is operated at a temperature of about 50° C. to about 70° C. The at least one first column is operated at a pressure of about 10 psig to about 100 psig.

The carbonaceous materials in the first column comprise activated carbon having an iodine number of at least 500 and a surface area of at least 900 $m^2/g$, carbon black having an iodine number of at least 500 and a surface area of at least 400 $m^2/g$, or carbon molecular sieves have a pore size of at least about 2 Å. The carbonaceous materials in the second column comprise activated carbon having an iodine number of at least 500 and a surface area of at least 900 $m^2/g$, carbon black having an iodine number of at least 500 and a surface area of at least 400 $m^2/g$, or carbon molecular sieves have a pore size of at least about 2 Å.

Aspect 34 is a method of producing trifluoroiodomethane ($CF_3I$). The method comprises providing a feedstock comprising trifluoroacetyl iodide (TFAI); providing the feedstock to a reactor to produce a trifluoroiodomethane product stream; and passing the trifluoroiodomethane product stream from the reactor through at least one column charged with carbonaceous materials to remove hydrogen iodide (HI), hydrogen triiodide ($HI_3$) and iodine ($I_2$) from the trifluoroiodomethane product stream. The at least one column is operated at a temperature of about 50° C. to about 70° C. The carbonaceous materials comprise activated carbon having an iodine number of at least 500 and a surface area of at least 900 $m^2/g$, carbon black having an iodine number of at least 500 and a surface area of at least 400 $m^2/g$, or carbon molecular sieves have a pore size of at least about 2 Å.

What is claimed is:

1. A method of producing trifluoroiodomethane ($CF_3I$), the method comprising:
   providing a feedstock comprising trifluoroacetyl iodide (TFAI);
   passing the feedstock through at least one column charged with carbonaceous materials to remove at least one of hydrogen iodide (HI), hydrogen triiodide ($HI_3$) and iodine ($I_2$) from the feedstock; and
   providing the feedstock to a reactor to produce a trifluoroiodomethane product stream.

2. The method of claim 1, wherein passing the feedstock through at least one column charged with carbonaceous materials comprises passing the feedstock through the at least one column immediately prior to providing the feedstock to a reactor.

3. The method of claim 1, wherein passing the feedstock through at least one column charged with carbonaceous materials comprises recirculating the feedstock through the at least one column before providing the feedstock to the reactor.

4. The method of claim 1, wherein the at least one column charged with carbonaceous materials includes at least two columns and passing the feedstock through at least one column charged with carbonaceous materials comprises recirculating the feedstock through one of the two columns and then passing the feedstock through the other of the two columns immediately prior to providing the feedstock to a reactor.

5. The method of claim 1, wherein the at least one column is operated at a temperature of about 0° C. to about 100° C.

6. The method of claim 1, wherein the at least one column is operated at a pressure of about 0 psig to about 300 psig.

7. The method of claim 1, wherein the carbonaceous materials are selected from the group consisting of: activated carbon, carbon black, and carbon molecular sieves.

8. The method of claim 7, wherein the carbonaceous materials comprise activated carbon having an iodine number of at least 500 and a surface area of at least 900 $m^2/g$.

9. The method of claim 7, wherein the carbonaceous materials comprise carbon black having an iodine number of at least 500 and a surface area of at least 400 m²/g.

10. The method of claim 7, wherein the carbonaceous materials comprise carbon molecular sieves have a pore size of at least about 2 Å.

11. The method of claim 1, wherein at least one column charged with carbonaceous materials is at least one first column, the method further comprising:
   passing the trifluoroiodomethane product stream from the reactor through at least one second column charged with carbonaceous materials to remove at least one of hydrogen iodide (HI), hydrogen triiodide ($HI_3$) and iodine ($I_2$) from the trifluoroiodomethane product stream.

12. The method of claim 11, wherein the at least one first column is operated at a temperature of about 0° C. to about 100° C. and the second column is operated at a temperature of about 0° C. to about 100° C.

13. The method of claim 11, wherein the at least one first column is operated at a pressure of about 0 psig to about 300 psig.

14. The method of claim 11, wherein the carbonaceous materials in the at least one second column are chosen from the group consisting of: activated carbon, carbon black, and carbon molecular sieves.

15. A method of producing trifluoroiodomethane ($CF_3I$), the method comprising:
   providing a feedstock comprising trifluoroacetyl iodide (TFAI) to a reactor to produce a trifluoroiodomethane product stream; and
   passing the trifluoroiodomethane product stream from the reactor through at least one column charged with carbonaceous materials to remove at least one of hydrogen iodide (HI), hydrogen triiodide ($HI_3$) and iodine ($I_2$) from the trifluoroiodomethane product stream.

16. The method of claim 15, wherein the at least one column is operated at a temperature of about 0° C. to about 100° C.

17. The method of claim 15, wherein the carbonaceous materials are chosen from the group consisting of: activated carbon, carbon black, and carbon molecular sieves.

18. The method of claim 17, wherein the carbonaceous materials comprise activated carbon having an iodine number of at least 500 and a surface area of at least 900 m²/g.

19. The method of claim 17, wherein the carbonaceous materials comprise carbon black having an iodine number of at least 500 and a surface area of at least 400 m²/g.

20. The method of claim 17, wherein the carbonaceous materials comprise carbon molecular sieves have a pore size of at least about 2 Å.

* * * * *